(12) United States Patent
Bolugoddu et al.

(10) Patent No.: US 8,063,074 B2
(45) Date of Patent: Nov. 22, 2011

(54) POLYMORPHIC FORMS OF ESOMEPRAZOLE SODIUM

(75) Inventors: Vijayabhaskar Bolugoddu, Hyderabad (IN); Amarnath Reddy Lekkala, Hyderabad (IN); Saurabh Shashikant Chitre, Mumbai (IN); Srinivas Reddy Mamilla, Secunderabad (IN); Venkata Annapurna Sasikala Cheemalapati, Visakhapatnam (IN); Siva Prasad Reddy Seerapu, Visakhapatnam (IN)

(73) Assignees: Dr. Reddy's Laboratories Limited, Hyderabad, Andhra Pradesh (IN); Dr. Reddy's Laboratories, Inc., Bridgewater, NJ (US)

( * ) Notice: Subject to any disclaimer, the term of this patent is extended or adjusted under 35 U.S.C. 154(b) by 1135 days.

(21) Appl. No.: 11/741,806

(22) Filed: Apr. 30, 2007

(65) Prior Publication Data

US 2007/0259921 A1 Nov. 8, 2007

Related U.S. Application Data

(60) Provisional application No. 60/746,385, filed on May 4, 2006, provisional application No. 60/894,089, filed on Mar. 9, 2007.

(30) Foreign Application Priority Data

Dec. 14, 2006 (IN) .......................... 2326/CHE/2006

(51) Int. Cl.
*A61K 31/4439* (2006.01)
*C07D 401/12* (2006.01)
(52) U.S. Cl. ..................... 514/338; 546/273.7
(58) Field of Classification Search ............... 546/273.7; 514/338
See application file for complete search history.

(56) References Cited

U.S. PATENT DOCUMENTS

| | | | |
|---|---|---|---|
| 5,693,818 A * | 12/1997 | Von Unge | 546/273.7 |
| 5,948,789 A * | 9/1999 | Larsson et al. | 514/299 |
| 6,143,771 A | 11/2000 | Lindberg | |
| 6,627,646 B2 * | 9/2003 | Bakale et al. | 514/322 |
| 6,875,872 B1 | 4/2005 | Lindberg | |
| 2005/0031696 A1 | 2/2005 | Kolbe | |

FOREIGN PATENT DOCUMENTS

| | | |
|---|---|---|
| EP | 1 020 460 A2 | 7/2000 |
| WO | WO 98/54171 A1 | 12/1998 |
| WO | WO03/089408 A2 | 10/2003 |
| WO | WO 2004/020436 A1 | 3/2004 |
| WO | WO 2004/046134 A2 | 6/2004 |
| WO | WO 2004/089935 A1 | 10/2004 |
| WO | WO 2005/054228 A1 | 6/2005 |
| WO | WO 2006/001753 A1 | 1/2006 |
| WO | WO 2006/001755 A1 | 1/2006 |

OTHER PUBLICATIONS

Chemical & Engineering News, Feb. 2003, 32-35.*
Brittain ed., "Polymorphism, etc.," NY:Marcel Dekker, Inc., 1999, 1-2, 183-226, 235-238.*
U.S. Pharmacopia #23, National Formulary #18, 1995, 1843-1844.*
Muzaffar et al., "Polymorphism and Drug Availability, etc.," J of Pharm. (Lahore), 1979, 1(1), 59-66.*
Jain et al., "Polymorphism in Pharmacy", Indian Drugs, 1986, 23(6) 315-329.*
Taday et al., "Using Terahertz, etc.," J of Pharm. Sci., 92(4), 2003, 831-838.*
Concise Encyclopedia Chemistry, NY: Walter de Gruyter, 1993, 872-873.*
Rowland & Tozer, "Clinical Pharmacokinetics, etc.," 1995, p. 123.*
Silverman, The Organic Chemistry of Drug Design and Drug Action, NY: Academic Press, 1993, 72-76.*
Ulicky. Comprehensive Dictionary of Physical Chemistry, NY: Prentice Hall, 1992, p. 21.*
Doelker, english translation of Ann. Pharm. Fr., 2002, 60: 161-176, pp. 1-39.*
Doelker, english translation of S.T.P, Pratiques (1999), 9(5), 399-409, pp. 1033.*
Otuska et al., "Effect of Polymorphic, etc.," Chem. Pharm. Bull., 47(6) 852-856 (1999).*
Cmu Pharmaceutical polymorphism, internet, p. 1-3 (2002) (print out Apr. 3, 2008).*
Singhal et al., "Drug Polymorphism, etc.," Advanced Drug Delivery reviews 56, p. 335-347 (2004).*
Caira, "Crystalline Polymorphism, etc.," Topics in Current Chemistry, 198, 163-208 (1998).*
Bernstein et al., "Polymorphism in Molecular Crystals", Oxford: Clarendon Press, 2002, pp. 117, 118 and 272.*
Davidovitch et al., "Dectection of Polymorphism, etc.," American Pharmaceutical Review, In: Russell Pub., 2004, 7(1), pp. 10, 12, 14, 16 and 100.*
Gavezzotti, Angelo, "Are Crystal Structures Predictable?", Acc. Chem. Res., 1994, 27, 309-314.
Gavezzotti, Angelo, "Ten years of experience in polymorph prediction: what next?", CrystEngComm, 2002, 4(61), 343-347.
Singhal, Dharmendra, "Drug polymorphism and dosage form design: a practical perspective," 2004, 56, 335-347.
Day, Graeme M., et al., (2006) "Investigating the latent polymorphism of maleic acid," Chemical Communications 1 (1): 54-56.
Thallapally, Praveen K., (2004) "Polymorphism of 1,3,5-Trinitrobenzene Induced by a Trisindane Additive," Angewandte Chemie International Edition, 43 (9): 1149-1155.

* cited by examiner

*Primary Examiner* — Patricia Morris
(74) *Attorney, Agent, or Firm* — Thomas C. McKenzie; Balaram Gupta; Robert A. Franks

(57) ABSTRACT

Polymorphic crystalline Forms J, K, L, M, and N of esomeprazole sodium.

2 Claims, 8 Drawing Sheets

POLYMORPHIC FORMS OF ESOMEPRAZOLE SODIUM

INTRODUCTION TO THE INVENTION

The present invention relates to crystalline forms of esomeprazole sodium and processes for their preparation. It also relates to a process for the preparation of stable esomeprazole compositions and other salts of esomeprazole, starting from esomeprazole sodium crystalline forms.

Esomeprazole is chemically known as (S)-5-methoxy-2[[(4-methoxy-3,5-dimethyl-2-pyridinyl)-methyl]sulfinyl]-1H-benzimidazole (hereinafter referred to by its adopted name "esomeprazole"), is the S-enantiomer of omeprazole, and has the structure of Formula I.

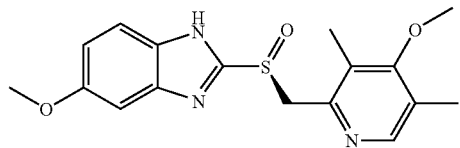

Formula I

Esomeprazole is a proton-pump inhibitor developed as an oral treatment for peptic ulcer, gastroesophageal reflux disease (GERD), duodenal ulcer and esophagitis.

Esomeprazole magnesium is available in the market under the brand name NEXIUM™ as delayed-release capsules for oral administration. Each delayed-release capsule contains 20 mg or 40 mg of esomeprazole (present as 22.3 mg or 44.5 mg esomeprazole magnesium trihydrate) in the form of enteric-coated pellets. Esomeprazole sodium is available as a sterile, freeze-dried, white to off-white, porous cake or powder in a 5 mL vial, intended for intravenous administration. NEXIUM™ I.V. for Injection contains esomeprazole sodium 21.3 mg or 42.5 mg, equivalent to esomeprazole 20 mg or 40 mg.

U.S. Pat. No. 6,143,771 discloses salts of esomeprazole and processes for their preparation, and U.S. Pat. No. 6,875,872 discloses esomeprazole magnesium and processes for its preparation.

International Application Publication No. WO 2003/089408 discloses alkali or alkaline earth metal salts of esomeprazole, including a sodium salt.

International Application Publication No. WO 2006/001755 discloses crystalline esomeprazole sodium Form B, and WO 2006/001753 discloses crystalline esomeprazole sodium Forms C, E & H.

The processes of the aforementioned documents for the preparation of esomeprazole sodium involve solvents that which are not preferred for pharmaceutical use.

International Application Publication No. WO 1998/54171 discloses a process for the preparation of the magnesium salt of the S-enantiomer of omeprazole trihydrate, wherein a potassium salt of S-omeprazole is used as an intermediate.

Various crystalline and amorphous forms of esomeprazole magnesium have also been described in International Application Publication Nos. WO 2004/046134, WO 2004/020436, and WO 2004/089935.

U.S. Patent Application Publication No. 2005/0031696 A1 describes a stabilized esomeprazole composition for use in pharmaceutical formulations.

Regulatory authorities throughout the world require that all possible crystalline forms of the same active drug compound be synthesized and characterized as completely as possible. There is thus a continuing need to prepare new polymorphic forms of pharmacologically active compounds of commercial interest such as esomeprazole or its salts, which provide the pharmaceutical formulation scientist with a broader spectrum of crystalline forms of an active ingredient to choose from, based on their differing physiochemical properties.

It is also important that the processes for the preparation of the polymorphic forms be robust and reproducible, so that the processes are easily scaled up in the plant.

The present invention provides crystalline forms of esomeprazole sodium and processes for their preparation, which are robust and reproducible.

SUMMARY OF THE INVENTION

The present invention relates to crystalline forms of esomeprazole sodium, and processes for their preparation. It also relates to a process for the preparation of stable esomeprazole compositions and other salts of esomeprazole, starting from esomeprazole sodium crystalline forms.

In certain aspects, the present invention provides crystalline Form J, Form K, Form L, Form M, and Form N of esomeprazole sodium, characterized by their X-ray powder diffraction ("XRPD") patterns, and processes for their preparation.

In an embodiment, a process for the preparation of Form J, Form K, Form L and Form M of esomeprazole sodium comprises:
a) providing a solution of esomeprazole;
b) reacting the solution of step a) with about 1 molar equivalent of a sodium base, per equivalent of esomeprazole; and
c) recovering the sodium salt of esomeprazole from a suitable solvent.

In another embodiment, a process for the preparation of crystalline esomeprazole sodium Form N comprises:
a) providing a solution of esomeprazole;
b) reacting the solution of step a) with about 1.5 molar equivalents of a sodium base, per equivalent of esomeprazole; and
c) recovering Form N of esomeprazole sodium from a suitable solvent.

In other aspects, the present invention provides esomeprazole sodium in amorphous form and a process for its preparation.

In a further aspect, the present invention provides a process for the preparation of stable esomeprazole compositions using esomeprazole sodium as a starting material.

In an embodiment, a process for the preparation of a stable esomeprazole composition using esomeprazole sodium as a starting material comprises:
a) converting esomeprazole sodium to esomeprazole;
b) adding one or more pharmaceutically acceptable stabilizers to a solution of esomeprazole; and
c) recovering a stable esomeprazole composition.

In a still further aspect, the present invention provides a process for the preparation of base addition salts of esomeprazole using esomeprazole sodium as starting material, which process comprises:
a) providing a solution of esomeprazole sodium in a suitable solvent;
b) reacting the solution of step a) with a suitable metal base; and
c) recovering an esomeprazole base addition salt.

Yet another aspect of the present invention provides a pharmaceutical composition comprising one or more of the crystalline Form J, Form K, Form L, Form M and Form N of esomeprazole sodium, or the amorphous form of esomeprazole sodium, or other esomeprazole salts prepared from esomeprazole sodium together with one or more pharmaceutically acceptable carriers, excipients or diluents.

An embodiment of the invention provides a process for preparing a crystalline form of esomeprazole sodium, comprising removing solvent from a solution of esomeprazole sodium in an alcohol and contacting a residue with a ketone.

Another embodiment of the invention provides a process for preparing a crystalline form of esomeprazole sodium, comprising crystallizing esomeprazole sodium from an alcohol, to form esomeprazole sodium having an X-ray diffraction pattern substantially in accordance with FIG. 3.

A further embodiment of the invention provides a process for preparing a crystalline form of esomeprazole sodium, comprising crystallizing esomeprazole sodium from a hydrocarbon to form esomeprazole sodium having an X-ray diffraction pattern substantially in accordance with FIG. 4.

An additional embodiment of the invention provides a process for preparing a crystalline form of esomeprazole sodium, comprising reacting a solution comprising esomeprazole with about 1.5 molar equivalents of a sodium base, per molar equivalent of esomeprazole, and adding an antisolvent or removing solvent to form esomeprazole sodium having an X-ray diffraction pattern substantially in accordance with FIG. 5.

A still further embodiment of the invention provides a process for preparing a stable composition comprising esomeprazole, comprising removing solvent from a solution comprising esomeprazole and at least one pharmaceutically acceptable stabilizer.

DETAILED DESCRIPTION OF THE INVENTION

The present invention relates to crystalline forms of esomeprazole sodium, and processes for their preparation. It also relates to a process for the preparation of stable esomeprazole compositions and other salts of esomeprazole, starting from esomeprazole sodium crystalline forms.

In one aspect, the present invention provides crystalline Form J, Form K, Form L, Form M and Form N of esomeprazole sodium characterized by their X-ray powder diffraction ("XRPD") patterns, and processes for their preparation:

The XRPD data reported herein were obtained using Cu Kα-1 radiation, having the wavelength 1.541 Å, and were generated using a Bruker AXS, D8 Advance Powder X-ray Diffractometer.

Figure 1:
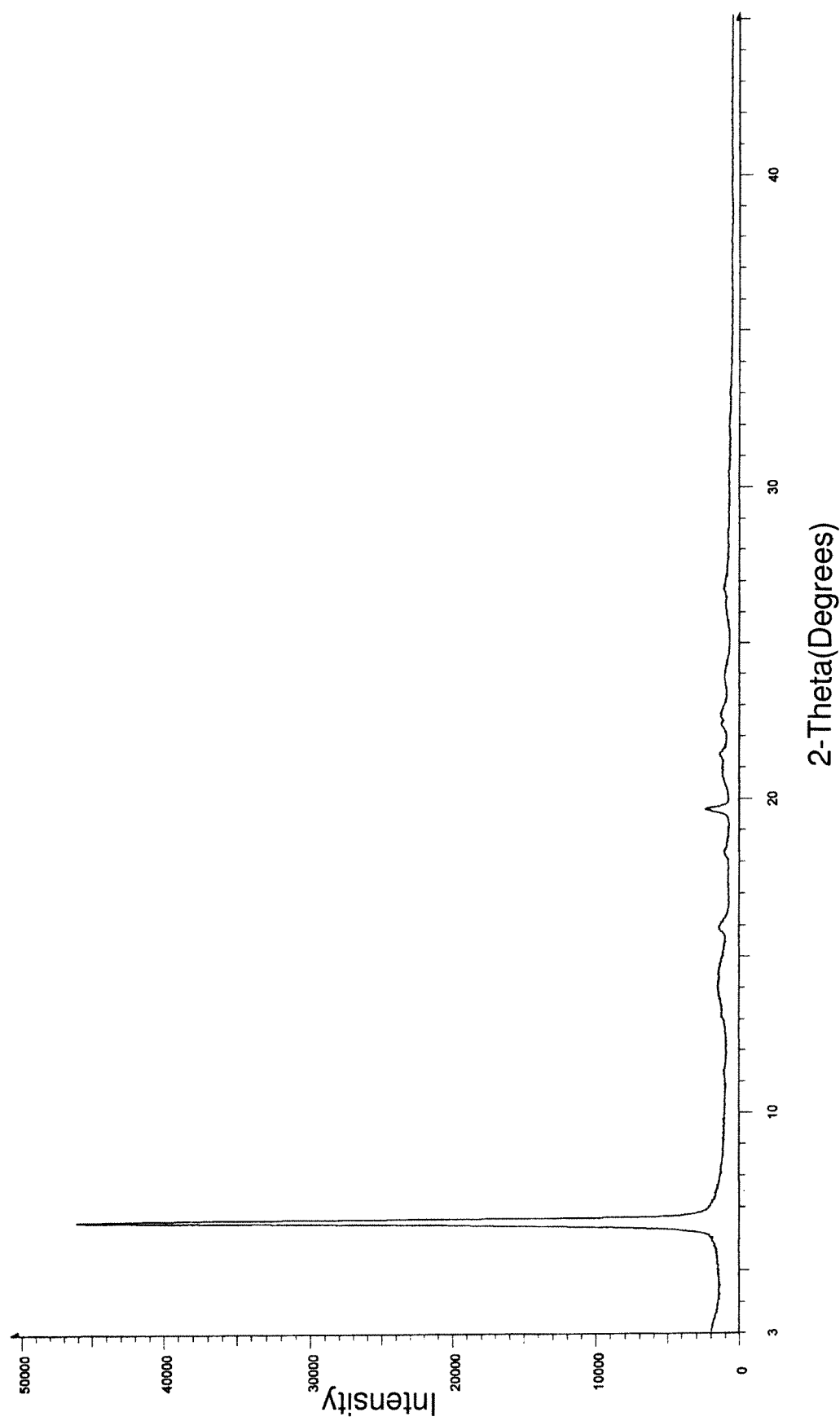
FIG. 1 is an X-ray powder diffraction pattern of esomeprazole sodium Form J prepared in Example 1.

The crystalline Form J of esomeprazole sodium is characterized by its XRPD pattern substantially in accordance with the pattern of FIG. 1. The crystalline Form J of esomeprazole sodium is also characterized by its XRPD pattern having significant peaks at about 6.5, 15.8, and 18.2, ±0.2 degrees 2θ. It is also characterized by the additional XRPD peaks at about 19.6 and 21.3, ±0.2 degrees 2θ.

Figure 2:
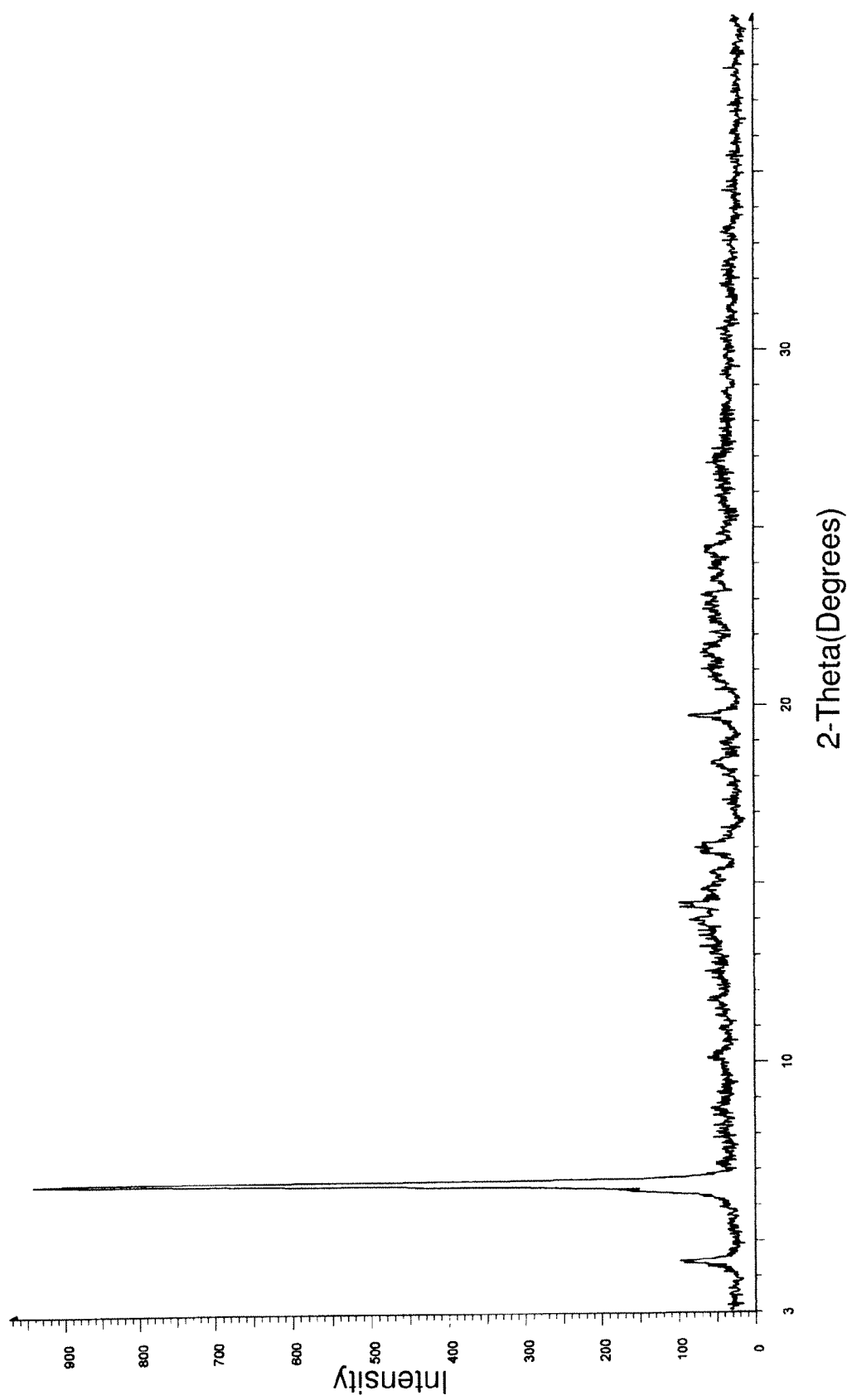
FIG. 2 is an X-ray powder diffraction pattern of esomeprazole sodium Form K prepared in Example 2.

The crystalline Form K of esomeprazole sodium is characterized by its XRPD pattern substantially in accordance with the pattern of FIG. 2. The crystalline Form K of esomeprazole sodium is also characterized by its XRPD pattern having significant peaks at about 6.5, 4.3, and 15.9, ±0.2 degrees 2θ. It is also characterized by the additional XRPD peaks at about 14.3 and 19.6, ±0.2 degrees 2θ.

Figure 3:
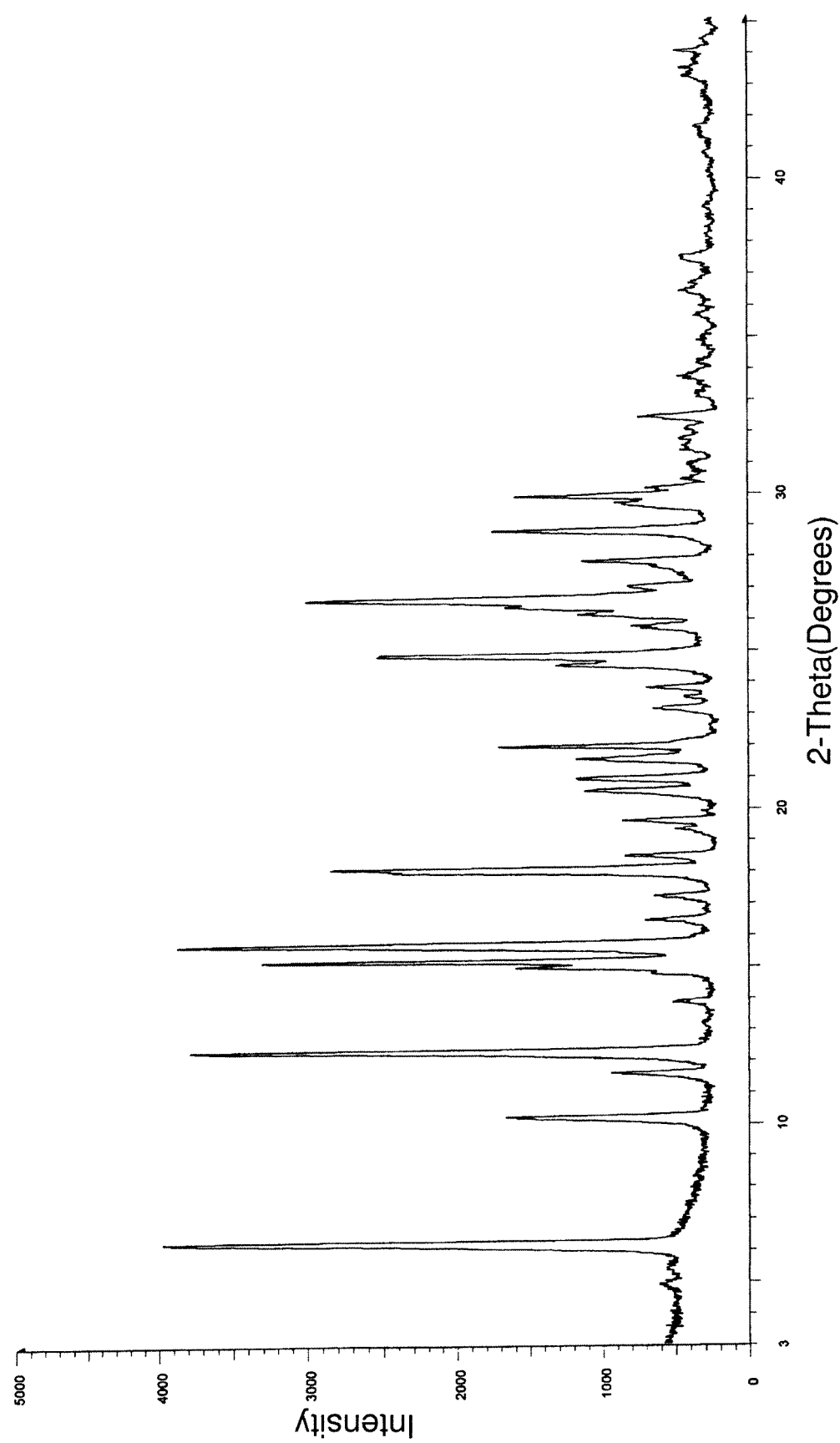
FIG. 3 is an X-ray powder diffraction pattern of esomeprazole sodium Form L prepared in Example 3.

The crystalline Form L of esomeprazole sodium is characterized by its XRPD pattern substantially in accordance with the pattern of FIG. 3. The crystalline Form L of esomeprazole sodium is also characterized by its XRPD pattern having significant peaks at about 6.1, 10.1, 12.2, 15.1, 15.6, 24.8, and 18.0, ±2 degrees 2θ. It is also characterized by the additional XRPD peaks at about 14.9, 20.9, 21.9, 26.3, and 29.9, ±0.2 degrees 2θ.

Figure 4:
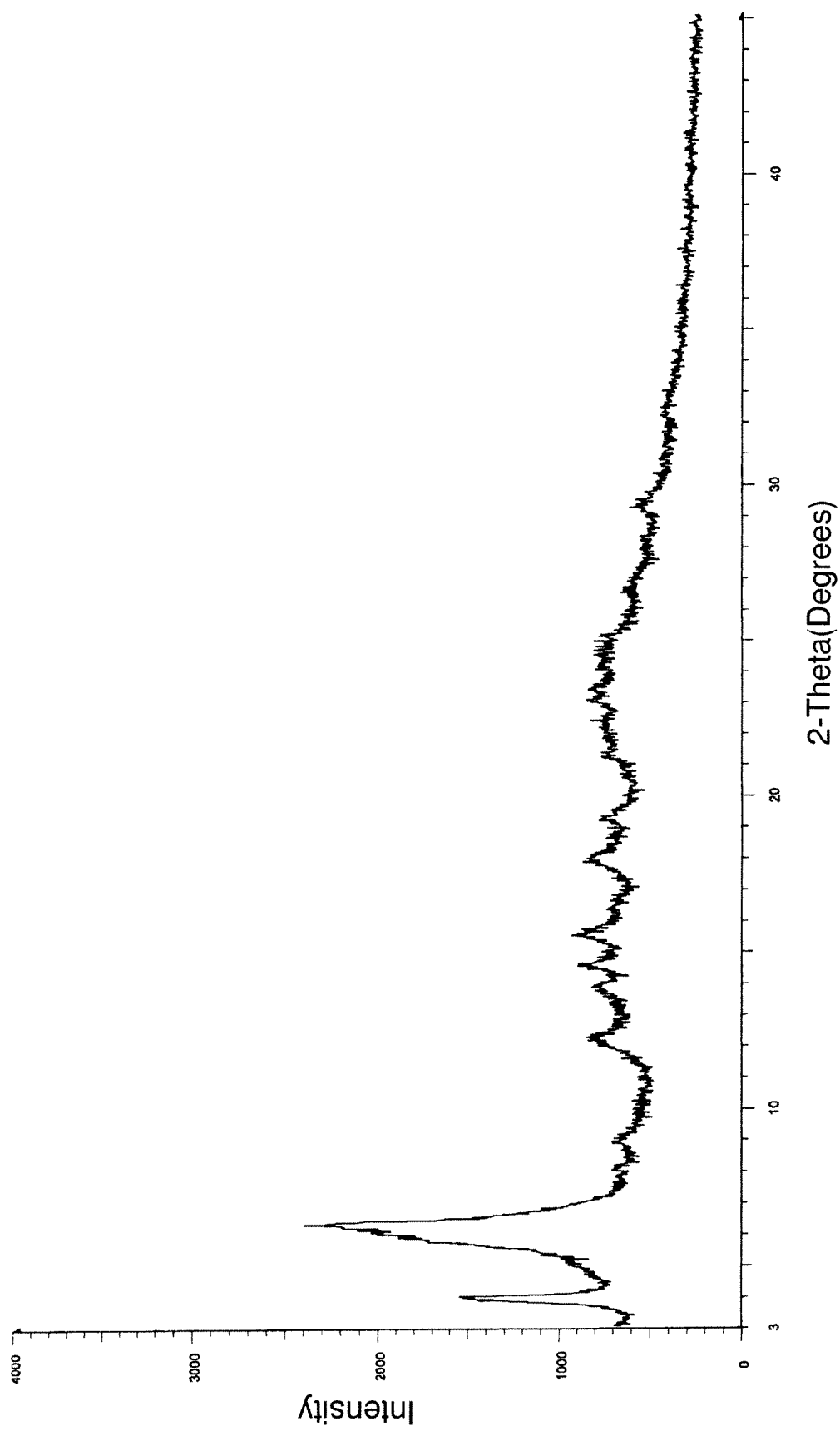
FIG. 4 is an X-ray powder diffraction pattern of esomeprazole sodium Form M prepared in Example 4

The crystalline Form M of esomeprazole sodium is characterized by its XRPD pattern substantially in accordance with the pattern of FIG. 4. The crystalline Form M of esomeprazole sodium is also characterized by its XRPD pattern having significant peaks at about 3.9, 5.8, 6.2, and 17.9, ±0.2 degrees 2θ. It is also characterized by the additional XRPD peaks at about 12.1, 14.5, and 15.5, ±0.2 degrees 2θ.

In an embodiment, the process for the preparation of esomeprazole sodium Form J, Form K Form L and Form M comprises:

a) providing a solution of esomeprazole;

b) reacting the solution of step a) with about 1 molar equivalent of a sodium base, per equivalent of esomeprazole; and c) recovering the sodium salt of esomeprazole from a suitable solvent.

Step a) involves providing a solution of esomeprazole.

The solution of esomeprazole may be obtained by dissolving esomeprazole in a suitable solvent, or the solution may be obtained directly from a reaction in which esomeprazole is formed.

When the solution is prepared by dissolving esomeprazole in a suitable solvent, any form of esomeprazole such as a crystalline or amorphous form, including any solvates or hydrates, may be utilized for preparing the solution.

Suitable solvents which can be used for preparation of the solution include, but are not limited to alcohols such as methanol, ethanol, propanol, tertiary-butanol, n-butanol and the like; ketones like acetone, methyl ethyl ketone, methyl isobutyl ketone and the like; nitrile solvents such as acetonitrile, propionitrile and the like; ester solvents such as ethyl acetate, propyl acetate and the like; chloro solvents like dichloromethane, 1,2-dichloroethane, chloroform, carbon tetrachloride and the like; hydrocarbon solvents such as toluene, xylene, n-heptane, cyclohexane, n-hexane and the like; dimethylformamide, dimethylsulphoxide, dioxane, tetrahydrofuran, water and the like; or mixtures thereof.

Suitably, the solution can be heated if clear dissolution is not obtained at ambient temperatures. The dissolution temperatures can range from about 20 to 120° C. depending on the solvent used for dissolution. Any other temperature is also acceptable as long as a clear solution of esomeprazole is provided.

The quantity of solvent used for dissolution depends on the solvent and the dissolution temperature adopted. The concentration of esomeprazole in the solution may generally range from about 0.1 to about 10 g/ml.

Step b) involves reacting the solution of step a) with about 1 molar equivalent of a sodium base, per equivalent of esomeprazole.

The solution of esomeprazole obtained in step a) can be treated with a suitable sodium compound to get esomeprazole sodium.

Suitable sodium bases which can be used include, but are not limited to, sodium methoxide, sodium hydroxide, sodium carbonate, sodium bicarbonate, and the like.

Suitably, the sodium base is used in the form of a solution, suitably, an aqueous or alcoholic solution, or a solution in a combination of methanol and water in various ratios.

When an alcohol or a combination of alcohol and water is used, suitable alcohols that can be used include, but are not limited to, $C_1$ to $C_5$ straight chain or branched chain alcohols such as methanol, ethanol, propanol, tertiary-butanol, and the like. The percentage of water while using a combination can vary from about 1 to about 99% by weight.

Optionally, the solution either in step a) or that obtained after treatment with the sodium compound in step b) is treated with carbon to remove any colored impurities, and to make the solution clear.

Step c) involves recovering the sodium salt of esomeprazole from a suitable solvent Esomeprazole sodium is recovered from the solution by suitable techniques such as antisolvent addition, or distillation followed by triturating with another suitable solvent.

The solution containing esomeprazole sodium is suitably distilled to get a residue. Distillation can be carried out by techniques such as evaporation, atmospheric distillation, or distillation under vacuum. Distillation may be conducted under a vacuum, such as below about 600 mm Hg to below about 100 mm Hg, at elevated temperatures such as about 20° C. to about 70° C. Any temperature and vacuum conditions can be used as long as there is no increase in the impurity levels of the product.

The solvent selected for isolation of the final product from the residue is important, since the solvent selected for the final isolation of the product should perform the functions of both eliminating the impurities and reducing crystallization time. It has been surprisingly found that isolation in different solvents provides different crystalline forms.

Suitable solvents which give Form J and Form K include but are not limited to: ketones such as acetone, butanone, ethyl methyl ketone and the like; chlorinated solvents such as dichloromethane, ethylenedichloride, chloroform and the like; and nitrile solvents such as acetonitrile, propionitrile and the like.

In one embodiment, ketone solvents were found to be useful for isolation of the final product with respect to elimination of impurities and providing fast crystallization.

Suitable solvents which give Form L include but are not limited to alcohols such as methanol, ethanol, isopropanol and the like, and mixtures thereof.

Suitable solvents which give Form M include but are not limited to hydrocarbons such as toluene, xylene and the like, and mixtures thereof.

The residual solvents in the residue are removed by co-distillation with another solvent. After the co-distillation solvent has been added to the residue obtained after distillation of the reaction solvent, the resulting system is distilled at between about 50° C. and about 98° C. using a Buchi Rotavapor, or any other distillation technique. Actual distillation temperature will vary according to the organic solvent used as a co-distillant and the percent of the reaction solvent present in the residue. Co-distillation is carried out until the percentage of the solvent used for preparation of the sodium salt is less than 5% by weight.

Isolation may be performed with stirring until the desired crystal yield has been obtained, such as for about one hour to about 72 hours, or longer. The crystallization step may further include facilitative measures known to one skilled in the art. For example, a crystallization step may further include cooling the solution, heating the solution, or adding an agent to induce precipitation.

The temperature of the solution may be brought down for crystallization to occur either rapidly using external cooling, or it may be allowed to cool by radiation without external cooling.

The obtained product is further dried and the duration of drying is a factor that determines the nature of the crystalline form obtained.

Typical drying temperatures range from about 30° C. to about 40° C.

When the duration of drying ranges from 0 hours to about 7 hours, esomeprazole sodium crystalline Form J is obtained, and when the duration of drying ranges from about 8 hours to about 15 hours, esomeprazole sodium crystalline Form K is obtained.

The moisture content of the Form J ranges from below about 5% to about 2% w/w, and for Form K ranges from above about 8% to about 10% w/w.

In a related aspect, the present invention provides crystalline esomeprazole sodium Form N and a process for its preparation.

Figure 5:
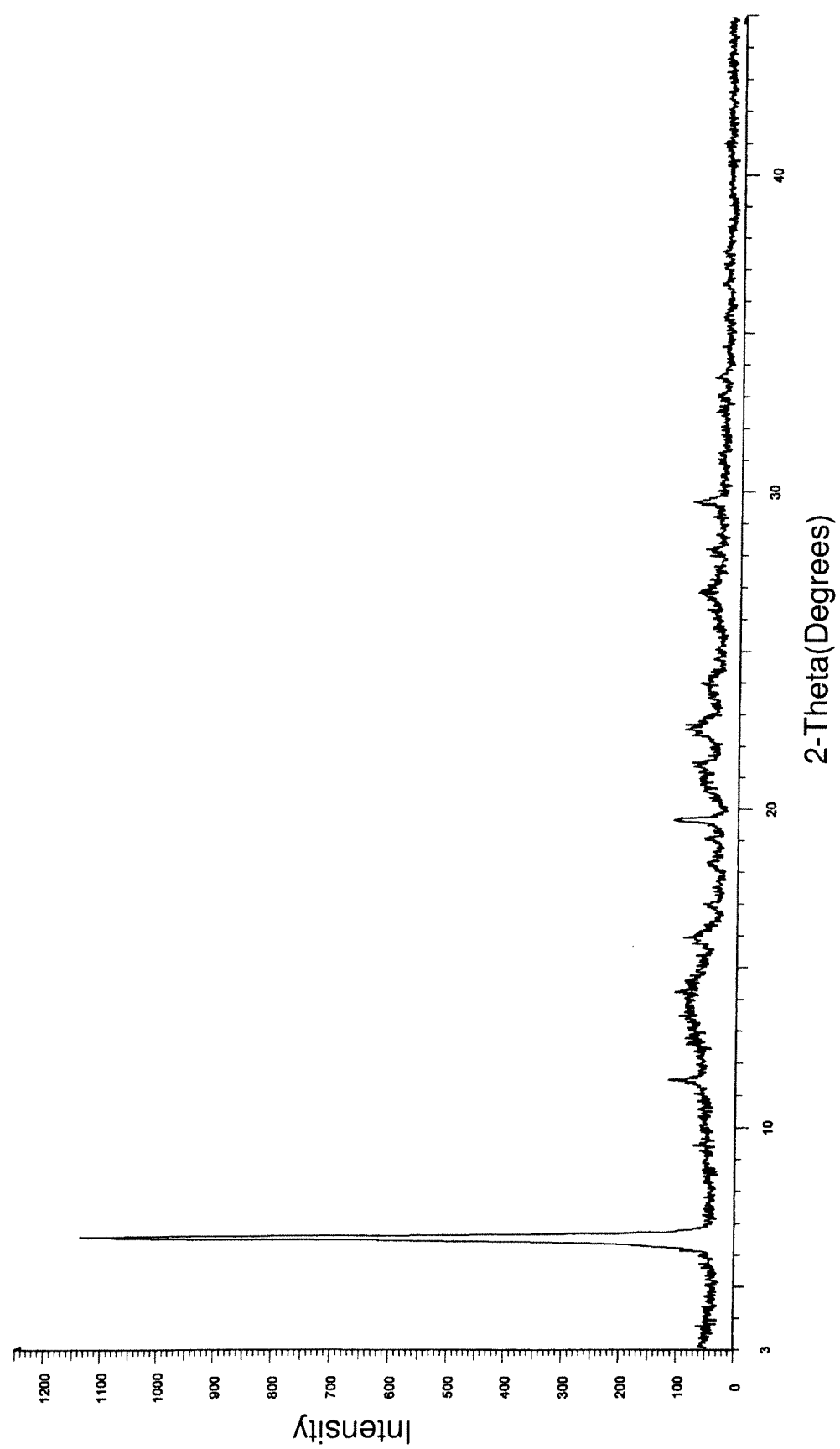
FIG. 5 is an X-ray powder diffraction pattern of esomeprazole sodium Form N prepared in Example 5

Crystalline esomeprazole sodium Form N is characterized by its XRPD pattern. The crystalline esomeprazole sodium Form N is characterized by its XRPD pattern substantially in accordance with the pattern of FIG. 5. The crystalline esomeprazole sodium Form N is also characterized by its XRPD pattern having significant peaks at about 6.3, 8.5, and 15.7, ±0.2 degrees 2θ. It is also characterized by the additional XRPD peaks at about 19.5 and 22.4, ±0.2 degrees 2θ.

In an embodiment, a process for the preparation of crystalline esomeprazole sodium Form N comprises:

a) providing a solution of esomeprazole;

b) reacting the solution of step a) with about 1.5 molar equivalents of sodium base, per equivalent of esomeprazole; and c) recovering the sodium salt of esomeprazole from a suitable solvent.

Step a) involves providing a solution of esomeprazole.

The solution of esomeprazole may be obtained by dissolving esomeprazole in a suitable solvent, or such a solution may be obtained directly from a reaction in which esomeprazole is formed.

When the solution is prepared by dissolving esomeprazole in a suitable solvent, any form of esomeprazole such as a crystalline or amorphous form, including any solvates or hydrates, may be utilized for preparing the solution.

Suitable solvents which can be used for preparation of the solution include, but are not limited to: alcohols such as methanol, ethanol, propanol, tertiary-butanol, n-butanol and the like; ketones like acetone, methyl ethyl ketone, methyl isobutyl ketone and the like; nitrile solvents such as acetonitrile, propionitrile and the like; ester solvents such as ethyl acetate, propyl acetate and the like; chloro solvents like dichloromethane, 1,2-dichloroethane, chloroform, carbon tetrachloride and the like; hydrocarbon solvents such as toluene, xylene, n-heptane, cyclohexane, n-hexane and the like dimethylformamide, dimethylsulphoxide, dioxane, water and the like; and mixtures thereof.

Suitably, the solution can be heated if clear dissolution is not obtained at ambient temperatures. The dissolution temperatures can range from about 20 to 120° C. depending on the solvent used for dissolution. Any other temperature is also acceptable as long as a clear solution of esomeprazole is provided.

The quantity of solvent used for dissolution depends on the solvent and the dissolution temperature adopted. The concentration of esomeprazole in the solution may generally range from about 0.1 to about 10 g/ml in the solvent.

Step b) involves reacting the solution of step a) with about 1.5 molar equivalents of sodium base, per equivalent of esomeprazole.

The solution of esomeprazole obtained in step a) can be treated with a suitable sodium compound to get esomeprazole sodium.

It has been surprisingly found that when 1.5 molar equivalents of sodium compound are used the crystalline form obtained is different from the previously known forms.

Suitable sodium bases that can be used include, but are not limited to, sodium methoxide, sodium hydroxide, sodium carbonate, sodium bicarbonate, and the like.

Suitably, the sodium compound is used as a solution, suitably, an aqueous or alcoholic solution, or a solution such as a combination of an alcohol and water in various ratios.

When an alcohol or a combination of alcohol and water is used, suitable alcohols which can be used include, but are not limited to $C_1$ to $C_5$ straight chain or branched chain alcohols such as methanol, ethanol, propanol, tertiary butanol, and the like. The percentage of water while using a combination can vary from about 1 to about 99% by weight.

Optionally, the solution either in step a) or that obtained after treatment with the sodium compound in step b) is treated with carbon to remove the colored impurities, and to make the solution clear.

Step c) involves recovering the sodium salt of esomeprazole from a suitable solvent.

Esomeprazole sodium is recovered from the solution by suitable techniques such as antisolvent addition or distillation followed by triturating with another suitable solvent.

The solution containing esomeprazole sodium is suitably distilled to get a residue. Distillation can be carried out by techniques such as evaporation, atmospheric distillation, or distillation under vacuum. Distillation may be conducted under a vacuum, such as below about 100 mm Hg to below about 600 mm Hg, at elevated temperatures such as about 20° C. to about 70° C. Any temperature and vacuum conditions can be used as long as there is no increase in the impurity levels of the product.

Suitably, after the distillation, the residue is co-distilled with the solvent that is used for isolation of the solid.

After the co-distillation solvent has been added to the residue obtained after distillation of the reaction solvent, the resulting system is distilled at between about 50° C. and about 98° C. using a Buchi Rotavapor, or any other distillation technique known to a person skilled in the art. Actual distillation temperature will vary according to the organic solvent used as a co-distillation agent and the percent of the reaction solvent present in the residue. Co-distillation is carried out till the percentage of the solvent used for preparation of the sodium salt is less than 5% by weight.

Esomeprazole sodium is recovered from the solution by suitable techniques such as anti-solvent addition, or distillation followed by triturating, or distillation followed by recrystallization with another suitable solvent.

Suitable solvents which can be used as anti-solvents or for triturating a residue to give Form N include but are not limited to ketones such as acetone, butanone, ethyl methyl ketone and the like; nitrile solvents such as acetonitrile, propionitrile and the like; ethers such as tetrahydrofuran (THF), dimethyl ether, diisopropyl ether and the like; ester solvents such as ethyl acetate, propyl acetate and the like; and mixtures thereof.

The isolation may be performed with stirring until the desired crystal yield has been obtained, such as for about one hour to about 72 hours, or longer. The crystallization step may further include facilitative measures known to one skilled in the art. For example, a crystallization step may further include cooling the solution, heating the solution, or adding an agent to induce precipitation.

The temperature of the solution may be brought down for crystallization to occur either rapidly using external cooling, or it may be allowed to cool to the isolation temperature by radiation. Generally, for large scale batches on the order of 1 to 5 kg or more, if the reaction mass is allowed to cool without external cooling, it may take a large amount of time, hence, external cooling is provided to the reaction mass to bring down its temperature to the required level.

The obtained product is further dried and the duration of drying determines the nature of the hydrate obtained. The drying temperature ranges from about 30° C. to about 40° C.

Crystalline forms of esomeprazole sodium prepared according to the process of the present invention have a particle size of $D_{90}$ less than about 200 μm.

The $D_{10}$, $D_{50}$ and $D_{90}$ values are useful ways for indicating a particle size distribution. $D_{90}$ refers to the value for the particle size for which at least 90 volume percent of the particles have a size smaller than the value. Likewise $D_{50}$ and $D_{10}$ refer to the values for the particle size for which 50 volume percent, and 10 volume percent, of the particles have a size smaller than the value. Methods for determining $D_{10}$, $D_{50}$ and $D_{90}$ include laser diffraction, such as using equipment sold by Malvern Instruments Ltd. of Malvern, Worcestershire, United Kingdom.

Crystalline forms of esomeprazole sodium prepared according to the present invention have a mean particle size of less than about 100 μm, $D_{10}$ less than about 20 μm, or less than about 50 μm, $D_{50}$ less than about 50 μm, or less than about 100 μm, and $D_{90}$ less than about 100 μm, or less than about 200 μm. There is no specific lower limit for any of the D values.

Yet another aspect of the present invention provides esomeprazole sodium in amorphous form and a process for its preparation.

Amorphous esomeprazole sodium can be characterized by its X-ray powder diffraction ("XRPD") pattern.

Figure 6:
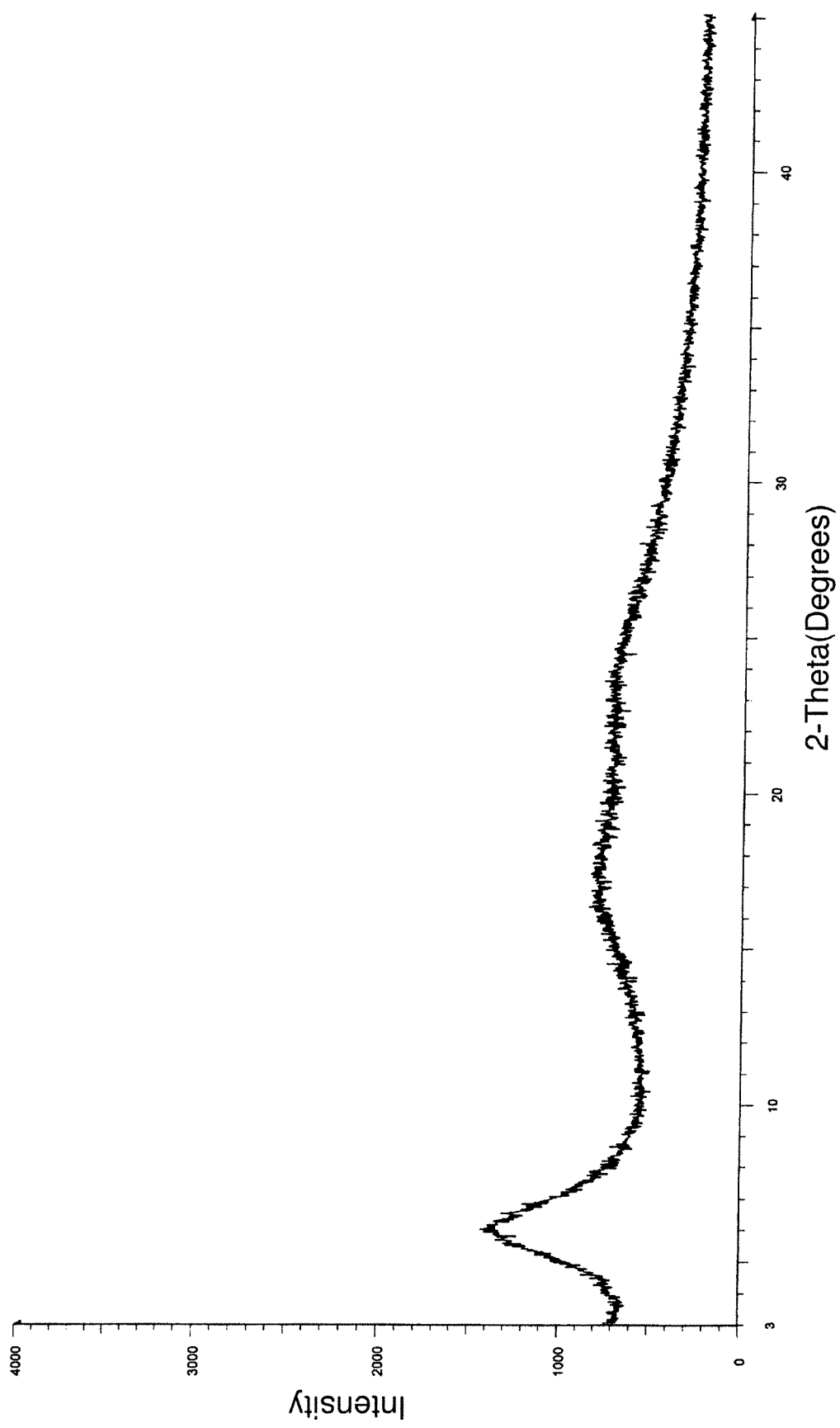
FIG. 6 is an X-ray powder diffraction pattern of amorphous esomeprazole sodium prepared in Example 6.

Amorphous esomeprazole sodium is characterized by its X-ray powder diffraction ("XRPD") pattern showing a plain halo with no peaks, which is characteristic of an amorphous solid, substantially in accordance with FIG. 6.

In an embodiment, a process for the preparation of esomeprazole sodium in amorphous form comprises:

a) providing a solution of esomeprazole sodium;
b) removing the solvent; and
c) optionally, drying the solid.

Step a) involves providing a solution of esomeprazole sodium.

The solution of esomeprazole sodium may be obtained by dissolving esomeprazole sodium in a suitable solvent, or such a solution may be obtained directly from a reaction in which esomeprazole sodium is formed.

When the solution is prepared by dissolving esomeprazole sodium in a suitable solvent, any form of esomeprazole sodium such as any crystalline form of esomeprazole sodium including any solvates or hydrates may be utilized for preparing the solution.

Suitable solvents which can be used for dissolving esomeprazole sodium include but are not limited to alcohols such as methanol, ethanol, isopropyl alcohol, n-propanol, and the like; halogenated hydrocarbons such as dichloromethane, 1,2-dichloroethane, chloroform, carbon tetrachloride and the like; ketones such as acetone, ethyl methyl ketone, methyl isobutyl ketone and the like; esters such as ethyl acetate, n-propyl acetate, n-butyl acetate, t-butyl acetate and the like; ethers such as diethyl ether, dimethyl ether, diisopropyl ether, 1,4-dioxane and the like; hydrocarbons such as toluene, xylene, n-heptane, cyclohexane, n-hexane and the like; nitriles such as acetonitrile, propionitrile and the like; or mixtures thereof or their combinations with water in various proportions.

These lists of solvents are merely representative of those that can be used, and the lists are not intended to be exhaustive.

The dissolution temperatures can range from about 20 to 120° C. depending on the solvent used for dissolution. Any other temperature is also acceptable as long as a clear solution of esomeprazole is provided.

The quantity of solvent used for dissolution depends on the solvent and the dissolution temperature adopted. The concentration of esomeprazole in the solution may generally range from about 0.1 to about 10 g/ml in the solvent. The solution may optionally be treated with materials such as carbon or sodium sulfate for clarification. Optionally, the solution obtained above can be filtered to remove the undissolved particles followed by further processing.

Step b) involves removal of the solvent from the solution obtained from step a), using a suitable technique.

Removal of the solvent may be carried out suitably using evaporation, flash evaporation, atmospheric distillation, or distillation under vacuum. Solvent removal is conducted rapidly, to avoid crystal formation.

Distillation of the solvent may be conducted under a vacuum, such as below about 100 mm Hg to below about 600 mm Hg, at elevated temperatures such as about 20° C. to about 70° C. Any temperature and vacuum conditions can be used as long as there is no increase in the impurity levels of the product.

Suitable techniques which can be used for the distillation include atmospheric distillation, flash evaporation or distillation under vacuum using a rotational evaporator device such as a Buchi Rotovapor, spray drying, agitated thin film drying ("ATFD"), and the like.

These techniques are applicable to both aqueous and organic solutions of esomeprazole. However, solutions using the more volatile organic solvents are preferred.

Techniques such as Buchi Rotovapor drying and dry distillation under vacuum, may be suitable for laboratory-scale processes such as for quantities less than about 100 g. Other techniques such as spray drying, flash evaporation, and ATFD are more suitable for industrial scale production with a batch size of at least about 100 g or about 1 kg, or greater.

The amorphous material obtained from step b) can be collected from the equipment using techniques such as by scraping, or by shaking the container.

Step c) involves an optional drying of the product obtained from step b) to afford the amorphous esomeprazole.

Drying can be carried out at reduced pressures, such as below about 200 mm Hg or below about 50 mm Hg, at temperatures such as about 35° C. to about 70° C. The drying can be carried out for any desired time period that achieves the desired result, such as times about 1 to 20 hours, or longer. Drying may also be carried out for shorter or longer periods of time depending on the final product specifications.

Drying can be suitably carried out in a tray dryer, vacuum oven, air oven, or using a fluidized bed drier, spin flash dryer, flash dryer and the like.

In a further aspect, the present invention provides a process for the preparation of stable esomeprazole compositions using esomeprazole sodium as a starting material.

In an embodiment, the process for the preparation of a stable esomeprazole compositions using esomeprazole sodium as a starting material comprises:

a) converting esomeprazole sodium to esomeprazole;
b) adding a pharmaceutically acceptable stabilizer to the solution of esomeprazole; and
c) recovering a stable esomeprazole composition.

Step a) involves conversion of the sodium salt of esomeprazole to esomeprazole.

The conversion can be carried out by treatment of esomeprazole sodium with a suitable acid. The treatment with acid can be carried out in a solution phase. The pH of the solution is adjusted in such as way that esomeprazole is made free from sodium, by adding acid until the pH is less than about 8, or about 7.

Esomeprazole sodium is suitably dissolved in water or a combination of water and an organic solvent. Suitable organic solvents which can be used include, but are not limited to: halogenated hydrocarbons such as dichloromethane, 1,2-dichloroethane, chloroform, carbon tetrachloride and the like; ketones such as acetone, ethyl methyl ketone, methyl isobutyl ketone and the like; esters such as ethyl acetate, n-propyl acetate, n-butyl acetate, t-butyl acetate and the like; and ethers such as diethyl ether, dimethyl ether, diisopropyl ether, 1,4-dioxane and the like.

Suitable acids which can be used for adjusting the pH include, but are not limited to inorganic acids such as hydrochloric acid, sulphuric acid, para-toluene sulfonic acid and the like; and organic acids such as acetic acid, oxalic acid, tartaric acid, formic acid and the like.

The solvent containing esomeprazole is suitably distilled to get a residue of esomeprazole, which is then dissolved in a solvent, or the organic or aqueous layer can be carried directly to step b).

Step b) involves adding a pharmaceutically acceptable stabilizer to a solution of esomeprazole obtained in step a).

When the esomeprazole was isolated in the form of a residue step a), it can be dissolved in a suitable solvent to obtain a solution.

The solution can be optionally treated with activated carbon at a pH of about 7 to about 9 to enhance the color of the compound followed by filtration through a medium such as a flux calcined diatomaceous earth (Hyflow) bed to remove the carbon.

The stabilizers that can be used for the preparation of stable esomeprazole compositions include but are not limited to: pharmaceutical hydrophilic carriers such as polyvinylpyrrolidone (homopolymers or copolymers of N-vinylpyrrolidone), gums, cellulose derivatives (including hydroxypropyl methylcellulose, hydroxypropyl cellulose and others), cyclodextrins, gelatins, hypromellose phthalate, starches, or starch derivatives such as sodium starch glycolate; sugars such as lactose, mannitol, sucrose, glucose, fructose, or aldose; crystalline bases such as meglumine, microcrystalline cellulose or other cellulose forms and derivatives; alkaline earth metal salts, such as phosphates; aluminosilicates such as bentonite or kaolin; inorganic oxides sugars, polyhydric alcohols, polyethylene glycol, polyethylene oxides, polyoxyethylene derivatives, polyvinyl alcohol, propylene glycol derivatives and the like. The use of mixtures of more than one of the pharmaceutical carriers to provide desired release profiles or for the enhancement of stability is within the scope of this invention. Also, all viscosity grades, molecular weights, commercially available products, their copolymers, and mixtures are all within the scope of this invention without limitation.

These lists of solvents and pharmaceutically acceptable carriers are merely representative of those that can be used, and the lists are not intended to be exhaustive.

Step c) involves recovering a stable esomeprazole composition.

Isolation of the stable esomeprazole composition from the solution of step b) can be done by processes known in the art. Suitable techniques include, but are not limited to, isolation with or without distillation, and distillation followed by triturating with a suitable solvent.

Distillation of the solvent may be conducted under a vacuum, such as below about 600 mm Hg to below about 100 mm Hg, at elevated temperatures such as about 20° C. to about 70° C. Any temperature and vacuum conditions can be used as long as there is no increase in the impurity levels of the product.

Suitable techniques which can be used for the distillation include distillation using a rotational evaporator device such as a Buchi Rotovapor, spray drying, agitated thin film drying ("ATFD"), and the like.

These techniques are applicable to both aqueous and organic solutions of esomeprazole. However, solutions using the more volatile organic solvents are preferred.

Techniques such as Buchi Rotovapor drying and dry distillation under vacuum may be suitable for laboratory-scale processes such as for quantities less than about 100 g. Other techniques such as spray drying and ATFD are more suitable for industrial scale production with a batch size of at least about 100 g or about 1 kg, or greater.

Suitable solvents which can be used for triturating or recrystallization of the residue obtained after distillation include, but are not limited to hydrocarbon solvents such as toluene, xylene, n-hexane, n-heptane, cyclohexane and the like; nitrile solvents such as acetonitrile, propionitrile and the like; and mixtures thereof in various proportions.

The composition obtained can be optionally further dried suitably using a tray dryer, vacuum oven, air oven, fluidized bed drier, spin flash dryer, flash dryer and the like. The drying can be carried out at temperatures of about 35° C. to about 70° C. The drying can be carried out for any desired time periods to achieve the desired product purity, times from about 1 to 20 hours, or longer, frequently being sufficient.

In an embodiment, a stable esomeprazole composition is a composition comprising esomeprazole, mannitol and meglumine. A stable composition of esomeprazole with mannitol and meglumine is prepared by obtaining a solution of esomeprazole from esomeprazole sodium, followed by addition of mannitol and meglumine. The resultant solution/suspension is then suitably distilled and the residue triturated in a suitable solvent to get the desired product.

The combination of mannitol and meglumine can range from about 40 to about 55% by weight in the final esomeprazole composition. The meglumine content in the combination of mannitol and meglumine can range from about 1 to about 10% by weight.

A stable esomeprazole composition is characterized by its XRPD pattern. The degree of crystallinity will vary depending on the stabilizers selected. If amorphous stabilizers such as povidone are used, the product will be amorphous.

Figure 7:
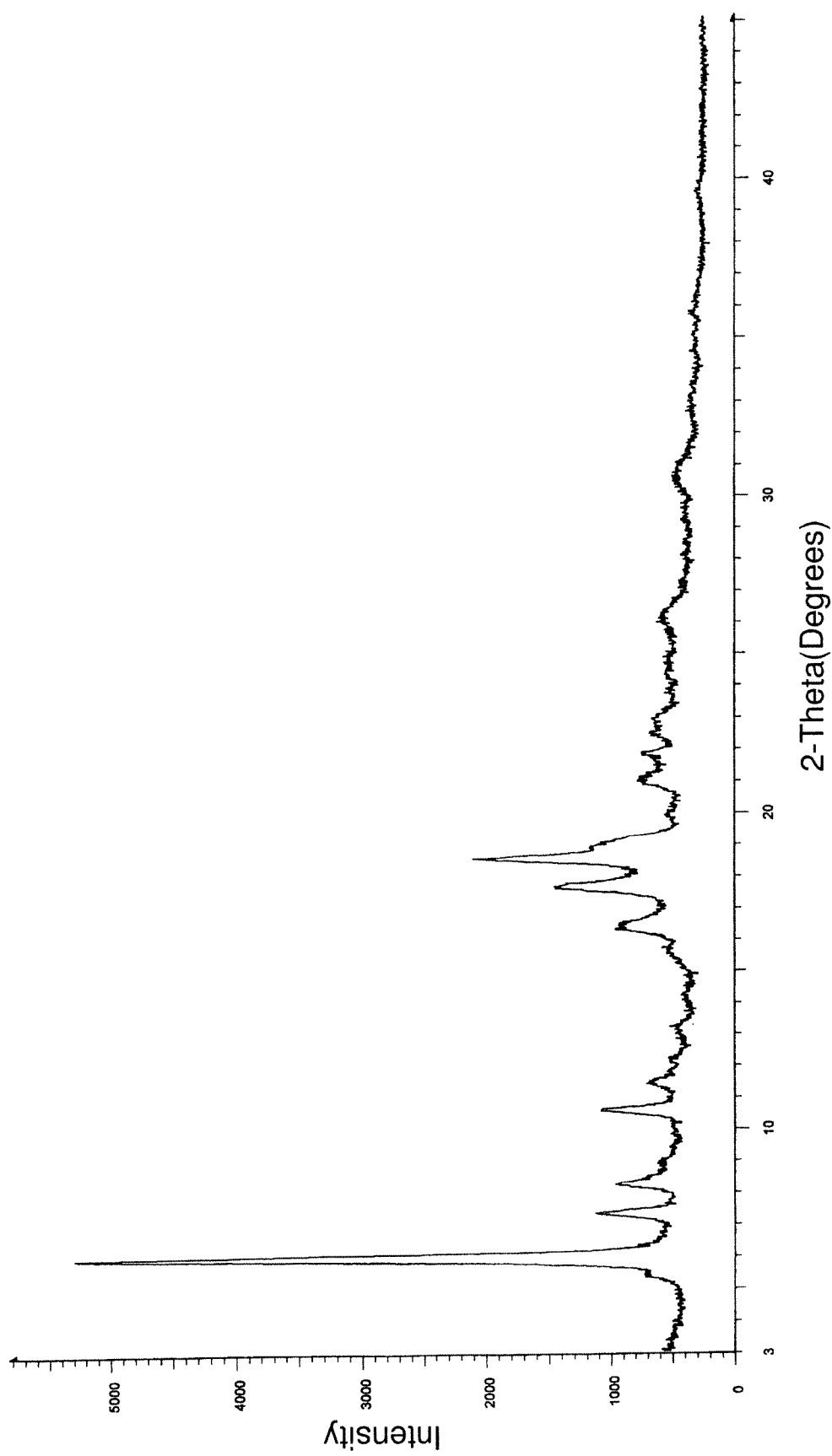
FIG. 7 is an X-ray powder diffraction pattern of esomeprazole magnesium prepared in Example 7.

The stable esomeprazole composition with mannitol and meglumine is characterized by its XRPD pattern substantially in accordance with the pattern of FIG. 7. The stable esomeprazole composition is also characterized by an XRPD pattern having significant peaks at about 23.3, 20.9, 20.3, and 14.5, ±0.2 degrees 2θ. It is also characterized by additional XRPD peaks at about 33.4, 38.6, and 44.0, ±0.2 degrees 2θ.

The XRPD peaks of the stable esomeprazole composition are attributed to the stabilizers used. The esomeprazole is amorphous and any crystallinity is due to the presence of the stabilizers.

Stable esomeprazole compositions obtained according to the process of the present invention have a $D_{90}$ of about 50 μm to about 200 μm.

In a still further aspect, the present invention provides a process for the preparation of other base addition salts of esomeprazole using esomeprazole sodium as starting material, which process comprises:

a) providing a solution of esomeprazole sodium in a suitable solvent;

b) reacting the solution of step a) with a suitable metal base; and c) recovering the esomeprazole base addition salt.

Step a) involves providing a solution of esomeprazole sodium.

The solution of esomeprazole sodium may be obtained by dissolving esomeprazole sodium in a suitable solvent, or such a solution may be obtained directly from a reaction in which esomeprazole sodium is formed.

When the solution is prepared by dissolving esomeprazole sodium in a suitable solvent, any form of esomeprazole sodium such as a crystalline or amorphous form, including any solvates or hydrates, may be utilized for preparing the solution.

Suitable solvents which can be used for preparation of the solution include, but are not limited to alcohols such as methanol, ethanol, propanol, tertiary-butanol, n-butanol; ketones like acetone, propanone; acetonitrile, dimethylformamide, dimethylsulphoxide, dioxane, and the like; esters such as ethyl acetate, n-propyl acetate, n-butyl acetate, t-butyl acetate and the like; nitriles such as acetonitrile, propionitrile and the like; halogenated hydrocarbons such as dichloromethane, 1,2-dichloroethane, chloroform, carbon tetrachloride and the like; water or mixtures thereof.

Suitably, the solution can be heated if clear dissolution is not obtained at ambient temperatures. The dissolution temperatures can range from about 20 to 120° C. depending on the solvent used for dissolution. Any other temperature is also acceptable as long as a clear solution of esomeprazole is provided.

The quantity of solvent used for dissolution depends on the solvent and the dissolution temperature adopted. The concentration of esomeprazole in the solution may generally range from about 0.1 to about 10 g/ml.

Step b) involves reacting the solution of step a) with a suitable metal base.

The solution obtained in step a) can be suitably treated with a desired metal compound for preparation of esomeprazole salts.

Compounds like magnesium sulfate, magnesium carbonate, magnesium acetate, magnesium hydroxide and the like can be used for the preparation of esomeprazole magnesium; and potassium hydroxide, potassium carbonate, potassium bisulfate can be used for preparation of esomeprazole potassium.

In an embodiment, the salt used is magnesium sulfate and the product is esomeprazole magnesium.

The magnesium salt of esomeprazole obtained by the process of present invention may be in crystalline or amorphous form that is characterized by XRPD pattern.

A crystalline magnesium salt of esomeprazole prepared by the process of the present invention is characterized by its X-ray powder diffraction ("XRPD") pattern.

Figure 8:
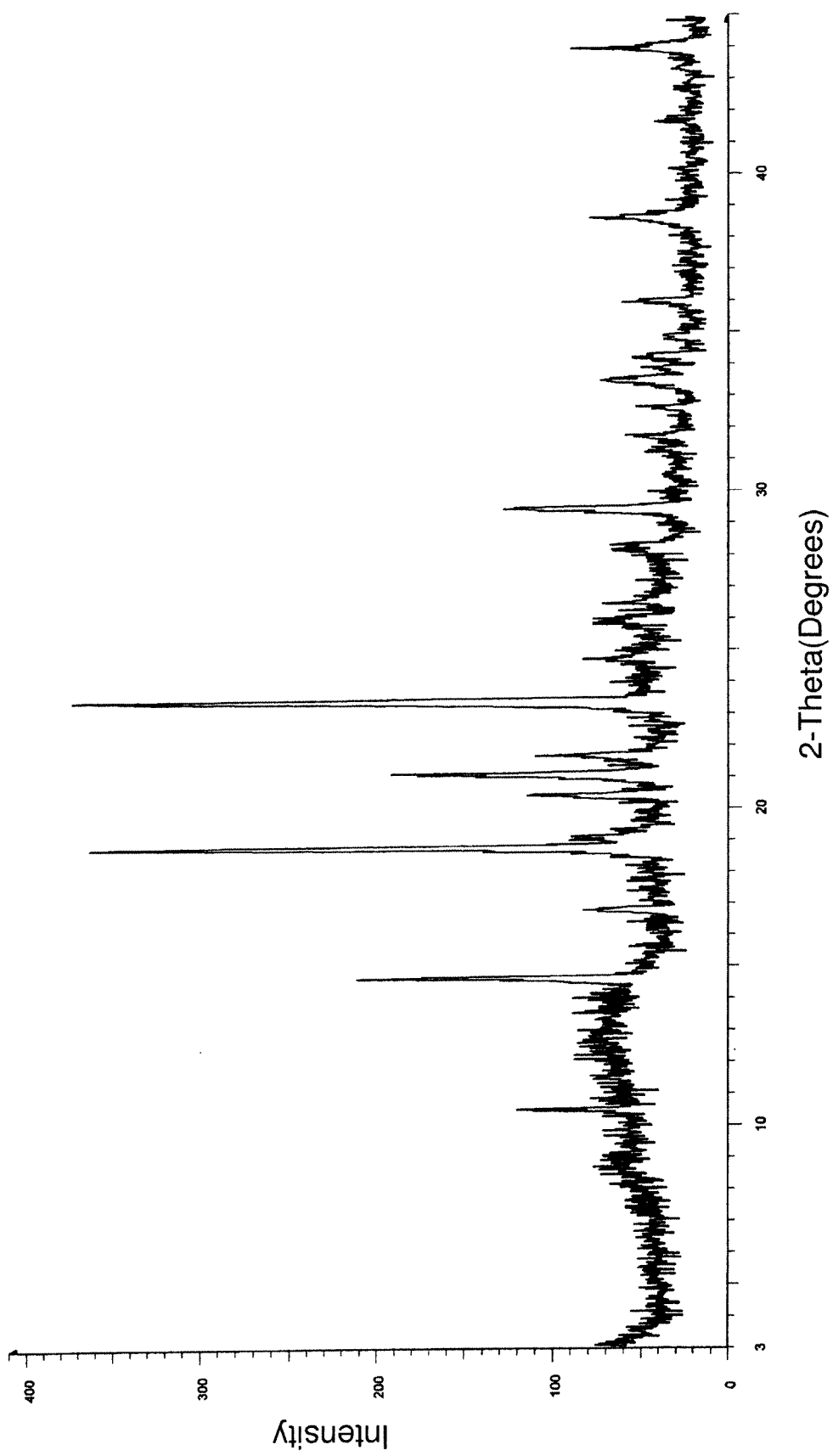
FIG. 8 is an X-ray powder diffraction pattern of a stable esomeprazole composition prepared in Example 8.

The crystalline magnesium salt of esomeprazole is characterized by its XRPD pattern substantially in accordance with the pattern of FIG. 8. The crystalline magnesium salt of esomeprazole is also characterized by an XRPD pattern having significant peaks at about 5.9, 7.3, 17.6, and 18.5, ±0.2 degrees 2θ. It is also characterized by the additional XRPD peaks at about 18.9 and 20.9, ±0.2 degrees 2θ.

In yet anther aspect, the present invention provides a pharmaceutical composition comprising one or more of crystalline Form J, Form K, Form L, Form M and Form N of esomeprazole sodium, together with one or more pharmaceutically acceptable carriers, excipients or diluents.

The pharmaceutical composition may be formulated as: solid oral dosage forms such as, but not limited to, powders, granules, pellets, tablets, and capsules; liquid oral dosage forms such as but not limited to syrups, suspensions, dispersions, and emulsions; and injectable preparations such as but not limited to solutions, dispersions, and freeze dried compositions. Formulations may be in the form of immediate release, delayed release or modified release. Further, immediate release compositions may be conventional, dispersible, chewable, mouth dissolving, or flash melt preparations, and modified release compositions that may comprise hydrophilic or hydrophobic, or combinations of hydrophilic and hydrophobic, release rate controlling substances to form matrix or reservoir or combination of matrix and reservoir systems. The compositions may be prepared by direct blending, dry granulation or wet granulation or by extrusion and spheronization. Compositions may be presented as uncoated, film coated, sugar coated, powder coated, enteric coated or modified release coated. Compositions of the present invention may further comprise one or more pharmaceutically acceptable excipients.

Pharmaceutically acceptable excipients that find use in the present invention include, but are not limited to: diluents such as starch, pregelatinized starch, lactose, powdered cellulose, microcrystalline cellulose, dicalcium phosphate, tricalcium phosphate, mannitol, sorbitol, sugar and the like; binders such as acacia, guar gum, tragacanth, gelatin, polyvinylpyrrolidone, hydroxypropyl cellulose, hydroxypropyl methylcellulose, pregelatinized starch and the like; disintegrants such as starch, sodium starch glycolate, pregelatinized starch, crospovidone, croscarmellose sodium, colloidal silicon dioxide and the like; lubricants such as stearic acid, magnesium stearate, zinc stearate and the like; glidants such as colloidal silicon dioxide and the like; solubility or wetting enhancers such as anionic or cationic or neutral surfactants; complex forming agents such as various grades of cyclodextrins, resins; release rate controlling agents such as hydroxypropyl cellulose, hydroxymethyl cellulose, hydroxypropyl methylcellulose, ethyl cellulose, methyl cellulose, various grades of methyl methacrylates, waxes and the like. Other pharmaceutically acceptable excipients that are of use include but are not limited to film formers, plasticizers, colorants, flavoring agents, sweeteners, viscosity enhancers, preservatives, antioxidants and the like.

Certain specific aspects and embodiments of this invention are described in further detail by the examples below, which examples are only illustrative and not intended to limit the scope of the appended claims in any manner

EXAMPLE 1

Preparation of Crystalline Esomeprazole Sodium Form J 50 ml of methanol was taken into a round bottom flask and a mixture of 12.75 g sodium hydroxide and 11 ml of water was added to it and stirred for clear dissolution at 31° C. 110 g of esomeprazole was dissolved in 550 ml of methanol and the solution was added to the above methanolic sodium hydroxide solution. The mass was subjected to stirring at a temperature of 30° C. for 40 minutes, followed by the addition of 5.5 g of carbon with simultaneous stirring. The reaction mass was filtered through a Celite bed, and washed with 550 ml of methanol. The filtrate was subjected to distillation at a temperature of 30° C. under a vacuum of 200 torr. The residue was co-distilled with 1650 ml of acetone in three equal lots at 35° C. To the obtained residue, 220 ml of acetone was added and stirred for one hour. The separated solid was filtered and dried at 34° C. for 12 hours to afford 61.5 g of the title compound.

Moisture content: 1.35% w/w.
Specific optical rotation $[\alpha]_D^{20}$=+43.220.
Purity by HPLC 99.99%.
Particle size distribution: $D_{10}$ less than 3 μm, $D_{50}$ less than 10 μm, $D_{90}$ less than 30 μm.
Bulk density: Before tapping: 0.428 g/ml.
After tapping: 0.630 g/ml.

EXAMPLE 2

Preparation of Crystalline Esomeprazole Sodium Form K 11.1 g of esomeprazole and 50 ml of methanol were taken in to a round bottom flask and stirred for 15 minutes. 1.0 g of carbon was added to the reaction mass and subjected to stirring for 30 minutes followed by filtration of the reaction mass through a Hyflow (flux calcined diatomaceous earth) bed. The filter bed was washed with 30 ml of methanol. The filtrate was transferred into a round bottom flask and stirred. 6 ml of aqueous sodium hydroxide was added to the filtrate and stirred for 40 minutes. Then the reaction mass was subjected to distillation under a vacuum of 100 torr at a temperature of 30° C. for 1 hour. The obtained residue was co-distilled with 150 ml of acetone in three equal lots under a vacuum of 200 torr and a temperature of 30° C. The residue obtained was taken into 200 ml of acetone and stirred for 30 minutes. The separated solid was filtered and washed with 20 ml of acetone. The wet solid was dried at a temperature of 34° C. for 7 hours to afford 54.5 g of the title compound.

Moisture content: 8.87% w/w.
Specific optical rotation: $[\alpha]_D^{20}$=+41.32°.

EXAMPLE 3

Preparation of Crystalline Esomeprazole Sodium Form L 3.47 g of sodium hydroxide and 105 ml of methanol were taken into a round bottom flask and stirred for dissolution. 30 g of esomeprazole was taken into a separate round bottom flask and dissolved in 150 ml of isopropanol and this solution was added to the above sodium hydroxide solution. The combined mixture was stirred for 1.5 hours, and distilled completely at 55° C. The residue was dissolved in 30 ml of isopropanol with stirring and the solution was cooled to 10° C. The mixture was stirred at 10° C. for 1 hour and filtered. The compound was dried at 34° C. for 5 hours to yield 10 g of the title compound.

EXAMPLE 4

Preparation of Crystalline Esomeprazole Sodium Form M 3.47 g of sodium hydroxide and 105 ml of methanol were taken into a round bottom flask and stirred for dissolution. 30 g of esomeprazole was taken into a separate round bottom flask and dissolved in 150 ml of toluene and this solution was added to the above sodium hydroxide solution. The combined mixture was stirred for 1.5 hours, and distilled completely at 55° C. The residue was then co-distilled with 450 ml of toluene in three equal lots. The residue was dissolved in 60 ml of toluene and stirred at 29° C. for 1 hour, 20 minutes and filtered. The solid was dried at 34° C. for 9 hours to yield 25.8 g of the title compound.

EXAMPLE 5

Preparation of Crystalline Esomeprazole Sodium Form N 8.7 g of sodium hydroxide and 175 ml of methanol were taken into a round bottom flask and stirred for 15 minutes. A solution of 50 g of esomeprazole dissolved in 175 ml of methanol was added to the above methanolic sodium hydroxide. The mixture was stirred at 29° C. for 3.5 hours. The mixture was then distilled atmospherically at 78° C. to remove 80% of the solvent. 250 ml of ethyl acetate was added to the residue and was co-distilled with 750 ml of ethyl acetate in three equal lots at 40° C. To the obtained residue, another 250 ml of ethyl acetate was added and stirred at 29° C. for 1 hour. The separated solid was filtered and washed with 100 ml of ethyl acetate. The wet compound was taken into another round bottom flask and 250 ml of ethyl acetate was added and stirred for 1 hour, 15 minutes. The separated solid was filtered and washed with 100 ml of ethyl acetate. The wet compound was dried at 62° C. for 6 hours to yield 51.2 g of the title compound.
Purity by HPLC: 99.78
R-isomer impurity: not detected.

EXAMPLE 6

Preparation of Amorphous Esomeprazole Sodium 2.31 g of sodium hydroxide and 70 ml of methanol were taken into a round bottom flask and stirred for dissolution. A solution of 20 g of esomeprazole in 70 ml of methanol was added to the above methanolic sodium hydroxide. The mixture was stirred at 30° C. for 3.5 hours. The mixture was then distilled using a flash distillation technique at 30° C. to obtain 16.8 g of the title compound.
Purity by HPLC: 99.38.
Moisture content: 2.72% w/w.

EXAMPLE 7

Preparation of Crystalline Esomeprazole Magnesium 50 g of esomeprazole sodium obtained according to the process described in Example 3 was taken into a round bottom flask and 400 ml of methanol was added. The mixture was stirred for 30 minutes at 29° C. for clear dissolution. After a clear dissolution was obtained, 30.2 g of magnesium sulfate was added and stirred for 3 hours at 30° C. The reaction mixture was filtered through a perlite bed and then treated with carbon. The carbon treated solution was distilled at a temperature of 40° C. and a pressure of 300 mm Hg to remove 90% of the solvent. 500 ml of acetone was added to the residue and stirred for 6 hours. The separated solid was filtered and washed with 100 ml of acetone. The wet solid was dried at 34° C. for 12 hours to yield 28 g of the title compound.
Purity by HPLC: 99.89
R-isomer impurity: 0.02%.

EXAMPLE 8

Preparation of a Crystalline Stable Esomeprazole Composition 40 g of esomeprazole sodium obtained in Example 3 and 400 ml of water were taken into a round bottom flask and stirred for clear dissolution. 200 ml of ethyl acetate was added to the solution and the pH was adjusted to 7.5 using 15% acetic acid solution. The organic layer was separated and the aqueous layer was extracted into 400 ml of ethyl acetate in two equal lots. The combined organic layer was washed with 200 ml of water. The organic layer was distilled completely under a vacuum of 300 mm Hg at a temperature of 34° C. To the residue, 200 ml of acetone was added and stirred for clear dissolution. After clear dissolution was obtained, the solution was treated with carbon. To the carbon-treated solution, 200 ml of water was added and stirred for 5 minutes. 26 g of mannitol and 2 g of meglumine were added to the solution and stirred for 25 minutes. 300 ml of cyclohexane was added to the reaction mass and the solvent was distilled completely using high vacuum distillation at a temperature of 29° C. To the residue 150 ml of acetone, 8 ml of water, and 300 ml of cyclohexane was added to the mass and again distilled using high vacuum distillation. To the residue obtained another 300 ml of cyclohexane was added and the solvent was completely distilled using high vacuum distillation. To the residue obtained, 120 ml of cyclohexane was added and stirred for 30 minutes at 29° C. The separated solid was filtered and washed with 90 ml of cyclohexane. The obtained solid was dried in a Buchi Rotavapor flask at 30° C. under a vacuum of 300 mm Hg to yield 56.1 g of the title composition.
Purity by HPLC: 99.65%.
Weight ratio of esomeprazole:mannitol:meglumine=50:47:3.

EXAMPLE 9

Conversion of Esomeprazole Sodium Crystalline Form J to Crystalline Form K 3.47 g of sodium hydroxide and 105 ml of methanol were taken into a round bottom flask and stirred at 29° C. A solution of 30 g of esomeprazole in 150 ml of dichloromethane was added to the above methanolic sodium hydroxide solution and stirred for 1 hour at 26° C. The mass was then distilled under a vacuum of 300 mm Hg at 38° C. The remaining residue was then co-distilled with 450 ml of dichloromethane in three equal lots. To the residue obtained, 60 ml of dichloromethane was added and stirred at 29° C. for 1.5 hours. The separated solid was filtered and washed with 30 ml of dichloromethane to give 32.2 g of Form J of esomeprazole sodium.

The crystalline Form J obtained above was further dried at 34° C. for 9 hours to yield 18.5 g of crystalline Form K of esomeprazole sodium.

EXAMPLE 10

Conversion of Esomeprazole Sodium Crystalline Form J to Crystalline Form K 3.47 g of sodium hydroxide and 105 ml of methanol were taken into a round bottom flask and stirred at 29° C. A solution of 30 g of esomeprazole in 150 ml of acetonitrile was added to the above methanolic sodium hydroxide solution and stirred for 1 hour at 26° C. The reaction mass was then distilled under a vacuum of 300 mm Hg at 38° C. The residue was then co-distilled with 450 ml of acetonitrile in three equal lots. To the residue obtained, 60 ml of dichloromethane was added and stirred at 29° C. for 1.5 hours. The separated solid was filtered and washed with 30 ml of acetonitrile to give 42.6 g of Form J of esomeprazole sodium.

The crystalline Form J obtained above was further dried at 34° C. for 9 hours to yield 25.6 g of crystalline Form K of esomeprazole sodium.

EXAMPLE 11

Preparation of Amorphous Esomeprazole Magnesium 40 g of esomeprazole sodium obtained according to the process described in Example 3 was taken into a round bottom flask and 400 ml of water was added. The mixture was stirred for 20 minutes at 29° C. for clear dissolution. After a clear solution was obtained, 20 g of magnesium sulfate dissolved in 200 ml of water was added to the reaction solution for about 1 hour and stirring continued for one more hour at 29° C. The separated solid was filtered and washed with 200 ml of water. The wet solid was dried at 64° C. for 6 hours to yield 70 g of the title compound.

We claim:
1. Crystalline Form N of esomeprazole sodium having an X-ray diffraction pattern substantially in accordance with FIG. 5.
2. A pharmaceutical composition comprising crystalline Form N of esomeprazole sodium of claim 1, and at least one pharmaceutically acceptable excipient; wherein the pharmaceutical composition is a solid oral dosage form; a liquid oral dosage form; or an injectable preparation as a dispersion.

* * * * *